United States Patent
Nakai et al.

(10) Patent No.: US 10,245,006 B2
(45) Date of Patent: Apr. 2, 2019

(54) COMPOSITION FOR ACOUSTIC-WAVE PROBE, AND SILICONE RESIN FOR ACOUSTIC-WAVE PROBE, ACOUSTIC-WAVE PROBE AND ULTRASONIC PROBE USING THE SAME, AS WELL AS DEVICE FOR MEASURING ACOUSTIC WAVE, ULTRASONIC DIAGNOSIS DEVICE, DEVICE FOR MEASURING PHOTO ACOUSTIC WAVE AND ULTRASONIC ENDOSCOPE

(71) Applicant: FUJIFILM Corporation, Tokyo (JP)

(72) Inventors: Yoshihiro Nakai, Kanagawa (JP);
Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 851 days.

(21) Appl. No.: 14/832,383

(22) Filed: Aug. 21, 2015

(65) Prior Publication Data
US 2016/0051228 A1    Feb. 25, 2016

(30) Foreign Application Priority Data

Aug. 22, 2014 (JP) .............................. 2014-169909

(51) Int. Cl.
| | |
|---|---|
| A61B 8/00 | (2006.01) |
| A61B 5/00 | (2006.01) |
| C08K 3/36 | (2006.01) |
| C08L 83/04 | (2006.01) |
| C08L 83/14 | (2006.01) |
| A61B 8/12 | (2006.01) |
| C08G 77/12 | (2006.01) |
| C08G 77/20 | (2006.01) |

(52) U.S. Cl.
CPC .......... *A61B 8/4494* (2013.01); *A61B 5/0095* (2013.01); *A61B 8/4272* (2013.01); *A61B 8/4444* (2013.01); *C08K 3/36* (2013.01); *C08L 83/04* (2013.01); *C08L 83/14* (2013.01); *A61B 8/12* (2013.01); *C08G 77/12* (2013.01); *C08G 77/20* (2013.01)

(58) Field of Classification Search
CPC .......... C08G 77/12; C08G 77/20; C08K 3/36
See application file for complete search history.

(56) References Cited

U.S. PATENT DOCUMENTS

| | | | | |
|---|---|---|---|---|
| 5,226,930 | A * | 7/1993 | Sasaki | ............... H01L 21/30625 106/287.11 |
| 6,444,740 | B1 * | 9/2002 | DeCato | .................... C08K 3/22 427/387 |
| 2017/0267904 | A1 * | 9/2017 | Nakayama | ............. C09J 183/04 |

FOREIGN PATENT DOCUMENTS

| | | |
|---|---|---|
| JP | 2009-72605 A | 4/2009 |
| JP | 2010-213983 A | 9/2010 |

OTHER PUBLICATIONS

Freeman (Silicones, Published for The Plastics Institute, ILIFEE Books Ltd. (1962) pp. 26-27).*

* cited by examiner

*Primary Examiner* — Kuo Liang Peng
(74) *Attorney, Agent, or Firm* — Sughrue Mion, PLLC

(57) ABSTRACT

A composition for an acoustic-wave probe, containing a polysiloxane mixture, in which the polysiloxane mixture contains: a polysiloxane having a vinyl group; a polysiloxane having at least two Si—H groups in the molecular chain thereof; and silica particles having an average primary particle size of less than 12 nm.

15 Claims, 1 Drawing Sheet

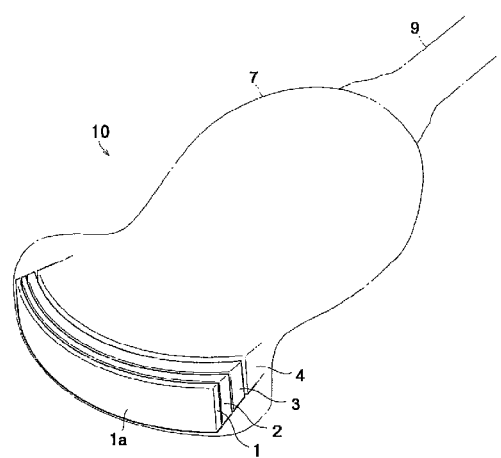

COMPOSITION FOR ACOUSTIC-WAVE PROBE, AND SILICONE RESIN FOR ACOUSTIC-WAVE PROBE, ACOUSTIC-WAVE PROBE AND ULTRASONIC PROBE USING THE SAME, AS WELL AS DEVICE FOR MEASURING ACOUSTIC WAVE, ULTRASONIC DIAGNOSIS DEVICE, DEVICE FOR MEASURING PHOTO ACOUSTIC WAVE AND ULTRASONIC ENDOSCOPE

CROSS-REFERENCE TO RELATED APPLICATION

The present application claims priority under 35 U.S.C. § 119 to Japanese Patent Application No. 2014-169909 filed in Japan on Aug. 22, 2014. The above application is hereby expressly incorporated by reference, in its entirety, into the present application.

TECHNICAL FIELD

A present invention relates to a composition for an acoustic-wave probe, and a silicone resin for an acoustic-wave probe, an acoustic-wave probe and an ultrasonic probe using the same. Further, the present invention relates to a device for measuring an acoustic wave, an ultrasonic diagnosis device, a device for measuring a photo acoustic wave and an ultrasonic endoscope.

BACKGROUND ART

In a device for measuring an acoustic wave, an acoustic-wave probe is used that receives a reflected wave (echo) generated by an acoustic wave irradiation to a target to be examined or a target site to be examined (hereinafter, simply referred to as a "target to be examined") and outputs a signal. The device for measuring an acoustic wave displays electric signals converted from the reflected wave that is received by the acoustic-wave probe as an image. Thereby, an interior portion of the target to be examined can be visualized and observed.

As to the acoustic wave, a wave having a suitable frequency is selected among an ultrasonic wave, a photo acoustic wave, and the like, in accordance with a target to be examined, a measuring condition and the like.

For example, in an ultrasonic diagnosis device, by transmitting an ultrasonic wave toward an interior portion of the target to be examined and then receiving a ultrasonic wave reflected on a tissue inside the target to be examined, the interior portion is displayed as an image. In a device for measuring photo acoustic wave, by receiving an acoustic wave radiated from the interior portion of the target to be examined, due to a photo acoustic effect, the interior portion is displayed as an image. The photo acoustic effect means a phenomena in which when a pulse of electromagnetic waves such as a visible light, a far-red light, and a microwave is irradiated to the target to be examined, the target to be examined absorbs the electromagnetic waves and produces heat and thermally expands whereby an acoustic wave (typically an ultrasonic wave,) is generated.

A device for measuring an acoustic wave conducts transmission and reception of the acoustic wave with a living body which is a target to be examined, and therefore it has been desired to meet the requirements such as consistency of acoustic impedance with the living body and reduction of acoustic wave attenuation quantity.

For example, a probe for an ultrasonic diagnosis device being one of acoustic-wave probes (also referred to as an ultrasonic probe) is provided with a piezoelectric element transmitting and receiving an ultrasonic wave, and an acoustic lens which contacts with a living body. The ultrasonic wave transmitted from the piezoelectric element is entered to the living body through the acoustic lens. If a difference in acoustic impedance (density×sonic speed) between the acoustic lens and the living body is large, an ultrasonic wave is reflected on the surface of the living body, so that the ultrasonic wave is not efficiently entered into the living body, and therefore it is difficult to obtain a high resolution. Further, in order to transmit and receive an ultrasonic wave with high sensitivity, it is desired that ultrasonic attenuation quantity of the acoustic lens is small.

Therefore, as one of acoustic lens materials, a silicone resin is primarily used, which is close to the acoustic impedance (1.4 to $1.7 \times 10^6$ kg/m²/sec) of the living body and has a small ultrasonic attenuation quantity.

For example, Patent Literature 1 and the like propose a composition for an acoustic lens in which a silicone-based rubber (polyorganosiloxane), a butadiene-based rubber, or the like as a major ingredient is blended with an inorganic filler such as silica and the like.

Further, the acoustic lens is used in contact with the target to be examined, and therefore a mechanical strength enough to withstand long-term use thereof is required. For such occasions, Patent Literature 2 proposes a composition containing a powder of a silicone rubber, ytterbium oxide, or the like and silica particles, as a composition for an acoustic lens which satisfies acoustic lens characteristics (acoustic impedance, ultrasonic attenuation quantity, mechanical strength, and the like).

CITATION LIST

Patent Literature

Patent Literature 1: JP-A-2010-213983 ("JP-A" means unexamined published Japanese patent application)
Patent Literature 2: JP-A-2009-72605

SUMMARY OF INVENTION

A composition for an acoustic-wave probe, containing a polysiloxane mixture,
  wherein the polysiloxane mixture contains:
  a polysiloxane having a vinyl group;
  a polysiloxane having at least two Si—H groups in the molecular chain thereof; and
  a silica having an average primary particle size of less than 12 nm, which composition is favorably used for a silicone resin for an acoustic-wave probe, an acoustic-wave probe, an ultrasonic probe, a device for measuring an acoustic wave, an ultrasonic diagnosis device, a device for measuring a photo acoustic wave, and an ultrasonic endoscope.

Technical Problem

A silicone resin itself is soft and has a low mechanical strength. Therefore, in order to improve hardness and mechanical strength thereof, inorganic fillers such as silica (also referred to as an inorganic filler), and a vinyl group-containing resin (also referred to as a reinforcing agent) is blended in combination with increase in the molecular weight of a silicone resin having vinyl groups at both terminals thereof. However, there was a problem that achievement of a required mechanical strength inevitably increases a use amount of the inorganic fillers and the vinyl group-containing resin with respect to the silicone resin, which results in a silicone resin having a large acoustic attenuation quantity by contraries.

Therefore, the conventional silicone resin is hard to satisfy all of high-resin hardness, high-mechanical strength, and low-acoustic attenuation quantity, at a high level.

In consideration of the above situation, the present invention is contemplated for providing: a composition for an acoustic-wave probe which is able to greatly improve hardness and mechanical strength of the silicone resin, while keeping acoustic attenuation quantity low, a silicone resin for an acoustic-wave probe, an acoustic-wave probe, a device for measuring an acoustic wave, and an ultrasonic diagnosis device, all of which uses the composition for the acoustic-wave probe.

Further, the present invention is contemplated for providing an acoustic-wave probe, which can use a capacitive micromachined ultrasonic transducer (cMUT) which has an insufficient sensitivity, as an ultrasonic diagnosis transducer array. Further, the present invention is contemplated for providing a composition for an acoustic-wave probe and a silicone resin for an acoustic-wave probe, which is able to improve sensitivity, in a device for measuring a photo acoustic wave which has so low sensitivity that observation of a deep portion of a human body is difficult because an amount of an ultrasonic wave generated by a photo acoustic wave is small. In addition, the present invention is contemplated for providing a composition for an acoustic-wave probe and a silicone resin for an acoustic-wave probe, which is able to improve sensitivity, in an ultrasonic endoscope which has so low sensitivity that improvement in sensitivity is difficult from the viewpoint of structure, physical property and process adequacy because a signal line cable is longer compared to one for the surface of the living body.

Solution to Problem

As a result of studies on a silicone resin for an acoustic-wave probe, the present inventors have found that the above problems of the present invention can be solved by incorporating silica particles having a specific average primary particle size (hereinafter, also simply referred to as a "silica") into a composition for an acoustic-wave probe, which may be used for preparing the silicone resin for an acoustic-wave probe.

The above problems of the present invention was solved by the following means.

<1> A composition for an acoustic-wave probe, comprising a polysiloxane mixture,
wherein the polysiloxane mixture comprises:
a polysiloxane having a vinyl group;
a polysiloxane having at least two Si—H groups in the molecular chain thereof; and
silica particles having an average primary particle size of less than 12 nm.

<2> The composition for an acoustic-wave probe described in the above item <1>,
wherein the polysiloxane mixture comprises from 0.1 to 30 parts by mass of the silica particles having an average primary particle size of less than 12 nm, in a total amount of 100 parts by mass of the polysiloxane mixture.

<3> The composition for an acoustic-wave probe described in the above item <1> or <2>,
wherein the polysiloxane mixture comprises, in a total amount of 100 parts by mass thereof: from 10 to 99.4 parts by mass of the polysiloxane having a vinyl group; and from 0.5 to 90 parts by mass of the polysiloxane having at least two Si—H groups in the molecular chain thereof.

<4> The composition for an acoustic-wave probe described in any one of the above items <1> to <3>,
wherein the silica particles having an average primary particle size of less than 12 nm has a surface treated with a silane compound.

<5> The composition for an acoustic-wave probe described in any one of the above items <1> to <4>,
wherein the silica particles having an average primary particle size of less than 12 nm has a surface treated with a trimethylsilylation agent.

<6> The composition for an acoustic-wave probe described in any one of the above items <1> to <5>,
wherein the polysiloxane having a vinyl group comprises a phenyl group.

<7> The composition for an acoustic-wave probe described in any one of the above items <1> to <6>,
wherein the polysiloxane having a vinyl group has a mass average molecular weight from 10,000 to 200,000.

<8> The composition for an acoustic-wave probe described in any one of the above items <1> to <7>,
wherein the polysiloxane having a vinyl group has a mass average molecular weight from 30,000 to 150,000.

<9> The composition for an acoustic-wave probe described in any one of the above items <1> to <8>,
wherein the polysiloxane having at least two Si—H groups in the molecular chain thereof comprises a phenyl group.

<10> The composition for an acoustic-wave probe described in any one of the above items <1> to <9>,
wherein the composition for an acoustic-wave probe comprises from 0.00001 to 0.01 parts by mass of platinum or a platinum compound, with respect to 100 parts by mass of the polysiloxane mixture.

<11> A silicone resin for an acoustic-wave probe, in which the composition for an acoustic-wave probe described in any one of the above items <1> to <10> is hardened.

<12> An acoustic-wave probe, comprising at least one selected from the group consisting of an acoustic lens and an acoustic matching layer, which comprise the silicone resin for an acoustic-wave probe described in the above item <11>.

<13> An ultrasonic probe, comprising:
a capacitive micromachined ultrasonic transducer as an ultrasonic transducer array; and
an acoustic lens comprising the silicone resin for an acoustic-wave probe described in the above item <11>.

<14> A device for measuring an acoustic wave, comprising the acoustic-wave probe described in the above item <12>.

<15> An ultrasonic diagnosis device, comprising the acoustic-wave probe described in the above item <12>.

<16> A device for measuring a photo acoustic wave, comprising an acoustic lens comprising the silicone resin for an acoustic-wave probe described in the above item <11>.

<17> An ultrasonic endoscope, comprising an acoustic lens comprising the silicone resin for an acoustic-wave probe described in the above item <11>.

In the explanation of the present invention, unless otherwise noted, when a plurality of groups having identical signs exist in a formula, these groups may be identical with or different from each other. Further, a group (for example, an alkyl group) to be specified in each group may be further substituted with a substituent. Further, a "Si—H group" means a group having three bonds "—" on a silicon atom. In the explanation of the present invention, these three unpaired electrons for binding are omitted for simplifying the description.

Moreover, in the explanation of the present invention, a numerical value range indicated using "to" means a range including the numerical values described before and after "to" as the lower limit and the upper limit.

The mass average molecular weight in the present invention, unless otherwise noted, is a value (polystyrene conversion) measured by gel permeation chromatography (GPC).

Advantageous Effects of Invention

The present invention is able to provide a composition for an acoustic-wave probe which is able to greatly improve hardness and mechanical strength of a silicone resin, while maintaining a low attenuation quantity of acoustic wave (particularly preferably ultrasonic wave); a silicone resin for an acoustic-wave probe, an acoustic-wave probe, a device for measuring an acoustic wave, and an ultrasonic diagnosis device, all of which uses the composition for the acoustic-wave probe.

Further, the present invention is able to provide an ultrasonic probe which uses cMUT as an ultrasonic diagnosis transducer array, and a silicone resin for an acoustic-wave probe, which is able to improve sensitivity of a device for measuring a photo acoustic wave and an ultrasonic endoscope.

It is assumed that these effects are due to silica having a small and specific average primary particle size which acts as a stopper of a fine crack generated when mechanical stress is applied to a silicone resin for an acoustic-wave probe. In particular, it is assumed that a distance between particles becomes short due to the small average primary particle size and as a result, such particles more effectively achieve a function as the stopper, and thereby a tear strength of the silicone resin is greatly improved.

It is considered that as a result, increase in acoustic attenuation quantity is suppressed and, hardness and mechanical strength of the silicone resin for an acoustic-wave probe are improved.

Other and further features and advantages of the invention will appear more fully from the following description, appropriately referring to the accompanying drawing.

BRIEF DESCRIPTION OF THE DRAWING

FIG. 1 is a perspective transmissive view of an example of a convex array ultrasonic probe that is one embodiment of an acoustic-wave probe.

DESCRIPTION OF EMBODIMENTS

<<Composition for Acoustic-wave Probe>>

The composition for an acoustic-wave probe (a probe for detecting an acoustic wave) (hereinafter, this composition is also referred to simply as a composition) of the present invention is a composition for an acoustic-wave probe containing a polysiloxane mixture in which a polysiloxane having a vinyl group, a polysiloxane having at least two Si—H groups in the molecular chain thereof, and silica particles having an average primary particle size of less than 12 nm are at least contained.

The content of the silica having an average primary particle size of less than 12 nm in a total amount of 100 parts by mass of the polysiloxane mixture is preferably from 0.1 to 30 parts by mass, more preferably from 1 to 25 parts by mass, and still more preferably from 5 to 20 parts by mass.

Further, the content of the polysiloxane having a vinyl group in a total amount of 100 parts by mass of the polysiloxane mixture is preferably from 10 to 99.4 parts by mass, and the content of the polysiloxane having at least two Si—H groups in the molecular chain thereof in a total amount of 100 parts by mass of the polysiloxane mixture is preferably from 0.5 to 90 parts by mass. The content of the polysiloxane having a vinyl group is more preferably from 50 to 90 parts by mass, and the content of the polysiloxane having at least two Si—H groups in the molecular chain thereof is more preferably from 1 to 50 parts by mass.

The polysiloxane mixture is a mixture having no catalyst which triggers a cross-linking polymerization (curing) of the polysiloxane having a vinyl group and the polysiloxane having at least two Si—H groups in the molecular chain thereof. Therefore, the silica particles having an average primary particle size of less than 12 nm are contained in the polysiloxane mixture but a catalyst is not contained therein.

The total amount 100 parts by mass of the polysiloxane mixture means that the individual content of ingredients contained in the polysiloxane mixture is 100 parts by mass.

Each of the above polysiloxanes contained in the polysiloxane mixture may be any polysiloxanes, as long as the polysiloxane has a vinyl group or at least two Si—H groups in the molecular chain thereof. In the present invention, however, the polysiloxanes are preferably a polyorganosiloxane (A) having a vinyl group and a polyorganosiloxane (B) having at least two Si—H groups in the molecular chain thereof.

Therefore, in the present invention, a composition is preferred, which composition contains, as an ingredient, at least a polyorganosiloxane (A) having a vinyl group, a polyorganosiloxane (B) having at least two Si—H groups in the molecular chain thereof, and silica particles (C) having an average primary particle size of less than 12 nm are contained in a polyorganosiloxane mixture.

A preferable embodiment is described in detail below, in which a polysiloxane mixture contains the polyorganosiloxane (A) having a vinyl group and the polyorganosiloxane (B) having at least two Si—H groups in the molecular chain thereof. However, each of the polysiloxanes contained in the polysiloxane mixture is not limited to each of the polyorganosiloxanes (A) and (B).

<Polyorganosiloxane (A) Having Vinyl Group>

The polyorganosiloxane (A) having a vinyl group (hereinafter, also referred to simply as a polyorganosiloxane (A)) used in the present invention has at least two vinyl groups in the molecular chain thereof.

Examples of the polyorganosiloxane (A) having a vinyl group include a polyorganosiloxane (a) having vinyl groups at least at both terminals of the molecular chain thereof (hereinafter, also referred to simply as a polyorganosiloxane (a)) and a polyorganosiloxane (b) having at least two —O—Si(CH$_3$)$_2$(CH=CH$_2$) groups in the molecular chain thereof (hereinafter, also referred to simply as a polyorganosiloxane (b)). Among them, a polyorganosiloxane (a) having vinyl groups at least at both terminals of the molecular chain thereof is preferred.

The polyorganosiloxane (a) is preferably of a straight chain shape, and the polyorganosiloxane (b) is preferably a polyorganosiloxane (b) in which —O—Si(CH$_3$)$_2$ (CH=CH$_2$) binds to Si atom which constitutes a main chain thereof.

The polyorganosiloxane (A) having a vinyl group is hydrosilylated by a reaction with a polyorganosiloxane (B) having at least two Si—H groups, for example, under the condition in which a platinum catalyst coexists. A cross-linking (curing) structure is formed by this hydrosilylation reaction (addition curing reaction).

The content of the vinyl group in the polyorganosiloxane (A) is not particularly limited. From the view point of forming adequate networks among ingredients contained in the composition for an acoustic-wave probe, the content of the vinyl group is for example, preferably from 0.01 to 5% by mole, and more preferably from 0.05 to 2% by mole.

Herein, the content of the vinyl group means a molar percent of a vinyl group-containing siloxane unit, provided that the total of units which constitute the polyorganosiloxane (A) is 100% by mole. For example, in a case where all Si atoms, of Si—O units which constitute a main chain and Si at the terminal, each has one vinyl group, the content of the vinyl group is 100% by mole.

Further, the polyorganosiloxane (A) preferably has a phenyl group. The content of the phenyl group in the polyorganosiloxane (A) is not particularly limited. From the view point of the mechanical strength of the silicone resin for an acoustic-wave probe, the content of the phenyl group is for example, preferably from 1 to 80% by mole, and more preferably from 2 to 40% by mole.

Herein, the content of the phenyl group means a molar percent of a phenyl group-containing siloxane unit, provided that the total of units which constitute the polyorganosiloxane (A) is 100% by mole. For example, in a case where all Si atoms, of Si—O units which constitute a main chain and Si at the terminal, each has one phenyl group, the content of the phenyl group is 100% by mole.

The unit means a Si—O unit which constitutes a main chain and Si at the terminals of the polyorganosiloxane.

A polymerization degree and a specific gravity are not particularly limited. From the viewpoint of improvement in mechanical properties, hardness, chemical stability and the like of the silicone resin for an acoustic wave probe to be obtained (hereinafter, also referred to simply as a silicone resin), the polymerization degree is preferably from 200 to 3,000, and more preferably from 400 to 2,000, and the specific gravity is preferably from 0.9 to 1.1.

From the viewpoint of mechanical strength, hardness and processing easiness, the mass average molecular weight of the polyorganosiloxane having a vinyl group is preferably from 10,000 to 200,000, more preferably from 30,000 to 150,000, and still more preferably from 45,000 to 120,000.

The mass average molecular weight can be measured, for example, by using HLC-8220 (trade name, GPC apparatus, manufactured by TOSOH CORPORATION) and RI detector with toluene (manufactured by Shonanwako corporation) as an eluant and with TSKgel (registered trade mark) G3000HXL and TSKgel (registered trade mark) G2000HXL as a column under the condition: temperature of 23° C.; and flow rate of 1 mL/min.

The kinematic viscosity at 25° C. is preferably 1×10$^{-5}$ to 10 m$^2$/s, more preferably 1×10$^{-4}$ to 1 m$^2$/s, and further preferably 1×10$^{-3}$ to 0.5 m$^2$/s.

The kinematic viscosity can be measured by using Ubbelohde viscometer (for example, trade name: SU, manufactured by SIBATA SCIENTIFIC TECHNOLOGY LTD.) at 25° C. according to JIS Z8803.

The polyorganosiloxane (a) having vinyl groups at least at both terminals of the molecular chain thereof is preferably a polyorganosiloxane represented by Formula (A).

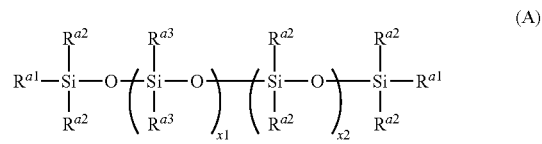

In Formula (A), R$^{a1}$ represents a vinyl group, and R$^{a2}$ and R$^{a3}$ each independently represent an alkyl group, a cycloalkyl group, an alkenyl group, or an aryl group. x1 and x2 each independently represent an integer of 1 or more. Herein, plural R$^{a2}$'s may be the same as or different from each other, and plural R$^{a3}$'s may be the same as or different from each other. Each group represented by R$^{a2}$ or R$^{a3}$ may be substituted with a substituent.

The number of carbon atoms of the alkyl group represented by any one of R$^{a2}$ and R$^{a3}$ is preferably 1 to 10, more preferably 1 to 4, further preferably 1 or 2, and particularly preferably 1. Examples of the alkyl group include methyl, ethyl, n-propyl, isopropyl, n-butyl, isobutyl, n-hexyl, n-octyl, 2-ethylhexyl, and n-decyl.

The number of carbon atoms of the cycloalkyl group represented by any one of R$^{a2}$ and R$^{a3}$ is preferably 3 to 10, more preferably 5 to 10, and further preferably 5 or 6. The cycloalkyl group is preferably a 3-membered ring, a 5-membered ring or a 6-membered ring; and more preferably a 5-membered ring or a 6-membered ring. Examples of the cycloalkyl group include cyclopropyl, cyclopentyl, and cyclohexyl.

The number of carbon atoms of the alkenyl group represented by any one of R$^{a2}$ and R$^{a3}$ is preferably 2 to 10, more preferably 2 to 4, and further preferably 2. Examples of the alkenyl group include vinyl, allyl, and butenyl.

The number of carbon atoms of the aryl group represented by any one of R$^{a2}$ and R$^{a3}$ is preferably 6 to 12, more preferably 6 to 10, and further preferably 6 to 8. Examples of the aryl group include phenyl, tolyl, and naphthyl.

These alkyl group, cycloalkyl group, alkenyl group and aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group and a cyano group.

Examples of the group having a substituent include a halogenated alkyl group.

R$^{a2}$ and R$^{a3}$ each are preferably an alkyl group, an alkenyl group or an aryl group; more preferably an alkyl group having 1 to 4 carbon atoms, a vinyl group or a phenyl group; and further preferably a methyl group, a vinyl group, or a phenyl group.

Among these, R$^{a2}$ is preferably a methyl group. R$^{a3}$ is preferably a phenyl group. Further, in the repeating unit to which x1 is attached, it is preferable that both of R$^{a3}$'s are a phenyl group.

x1 is preferably an integer of from 1 to 3,000, more preferably an integer of from 5 to 1,000.

x2 is preferably an integer of from 1 to 3,000, more preferably an integer of from 40 to 1,000.

Examples of the polyorganosiloxane having vinyl groups at least at both terminals of the molecular chain thereof include DMS-series (e.g., DMS-V31, DMS-V31S15, DMS-V33, DMS-V35, DMS-V35R, DMS-V41, DMS-V42, DMS-V46, DMS-V51 and DMS-V52), and PDV-series (e.g., PDV-0341, PDV-0346, PDV-0535, PDV-0541, PDV-1631, PDV-1635, PDV-1641, PDV-2335), PMV-9925, PVV-3522, FMV-4031 and EDV-2022, all of which are trade names and manufactured by Gelest, Inc.

In DMS-V31S15, fumed silica is preliminarily blended and therefore kneading by a particular machine is not required.

As to the polyorganosiloxane (A) having a vinyl group in the present invention, only one kind thereof may be used alone or at least two kinds thereof may be used in combination.

<Polyorganosiloxane (B) Having at Least Two Si—H Groups in Molecular Chain Thereof>

The polyorganosiloxane (B) having at least two Si—H groups in the molecular chain thereof used in the present invention (hereinafter, also referred to simply as a polyorganosiloxane (B)) has at least two Si—H groups in the molecular chain thereof.

The presence of at least two Si—H groups in the molecular chain allows cross-linking with a polyorganosiloxane having at least two vinyl groups.

The polyorganosiloxane (B) may have a straight-chain structure or a branched structure, and the straight-chain structure is preferred.

The mass-average molecular weight of the straight-chain structure is preferably from 500 to 100,000, and more preferably from 1,500 to 50,000, from the viewpoint of mechanical strength and hardness.

Further, the polyorganosiloxane (B) preferably has a phenyl group. The content of the phenyl group in the polyorganosiloxane (B) is not particularly limited. From the view point of the mechanical strength of the silicone resin for an acoustic-wave probe, the content of the phenyl group is for example, preferably from 20 to 80% by mole, and more preferably from 30 to 70% by mole.

Herein, the content of a phenyl group is a content calculated by replacing the polyorganosiloxane (A) with the polyorganosiloxane (B) in the content of the phenyl group of the polyorganosiloxane (A).

The equivalent amount of the polyorganosiloxane (B) is preferably 1,300 g/mol or less, more preferably 500 g/mol or less. On the other hand, the equivalent amount is preferably 50 g/mol or more, more preferably 100 g/mol or more.

In the present invention, both of the polyorganosiloxanes (A) and (B) preferably have a phenyl group for improving the compatibility of each other.

It is preferable that by incorporating a bulky phenyl group into the silicone resin for an acoustic-wave probe of the present invention, the sonic speed, the hardness and the specific gravity thereof can be enhanced. As a result, acoustic impedance can be enhanced.

The straight-chain structured polyorganosiloxane (B) having at least two Si—H groups in the molecular chain thereof is preferably a polyorganosiloxane represented by the following Formula (B).

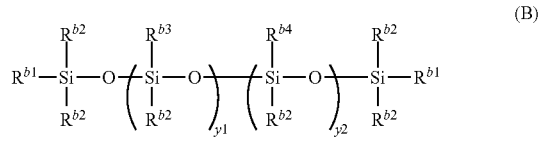
(B)

In Formula (B), $R^{b1}$ and $R^{b2}$ each independently represent a hydrogen atom, an alkyl group, a cycloalkyl group, an aryl group, or —O—Si($R^{b6}$)$_2$($R^{b5}$). $R^{b5}$ and $R^{b6}$ each independently represent a hydrogen atom, an alkyl group, a cycloalkyl group, or an aryl group. $R^{b3}$ and $R^{b4}$ each independently represent a hydrogen atom, an alkyl group, a cycloalkyl group, an alkenyl group, an aryl group, or —O—Si($R^{b8}$)$_2$($R^{b7}$). $R^{b7}$ and $R^{b8}$ each independently represent a hydrogen atom, an alkyl group, a cycloalkyl group, an alkenyl group, or an aryl group. y1 represents an integer of 0 or more. y2 represents an integer of 1 or more. Herein, plural $R^{b1}$'s may be the same as or different from each other, plural $R^{b2}$'s may be the same as or different from each other, plural $R^{b3}$'s may be the same as or different from each other, plural $R^{b4}$'s may be the same as or different from each other, plural $R^{b5}$'s may be the same as or different from each other, plural $R^{b6}$'s may be the same as or different from each other, plural $R^{b7}$'s may be the same as or different from each other, and plural $R^{b8}$'s may be the same as or different from each other. Each group represented by any one of $R^{b1}$ to $R^{b8}$ may be substituted with a substituent. However, at least two Si—H groups are present in the molecular chain.

The alkyl group and the cycloalkyl group represented by any one of $R^{b1}$ and $R^{b2}$ each have the same meaning as the alkyl group and the cycloalkyl group represented by any one of $R^{a2}$ and $R^{a3}$, and preferable ranges thereof are also the same. The alkyl group, the cycloalkyl group, and the alkenyl group represented by any one of $R^{b3}$ and $R^{b4}$ each have the same meaning as the alkyl group, the cycloalkyl group, and the alkenyl group represented by any one of $R^{a2}$ and $R^{a3}$, and preferable ranges thereof are also the same. The number of carbons of the aryl group represented by any one of $R^{b1}$ to $R^{b4}$ is preferably 6 to 12, more preferably 6 to 10, particularly preferably 6 to 8. The examples of the aryl group include a phenyl group, a tolyl group, and a naphthyl group.

The alkyl group, the cycloalkyl group, and the aryl group, represented by any one of $R^{b5}$ and $R^{b6}$ in —O—Si($R^{b6}$)$_2$($R^{b5}$) each have the same meaning as the alkyl group, the cycloalkyl group, and the aryl group represented by any one of $R^{b1}$ and $R^{b2}$, and preferable ranges thereof are also the same.

The alkyl group, the cycloalkyl group, the alkenyl group and the aryl group represented by any one of $R^{b7}$ and $R^{b8}$ in —O—Si($R^{b8}$)$_2$($R^{b7}$) each have the same meaning as the alkyl group, the cycloalkyl group, the alkenyl group and the aryl group represented by any one of $R^{b3}$ and $R^{b4}$, and preferable ranges thereof are also the same.

$R^{b1}$ and $R^{b2}$ each are preferably a hydrogen atom, an alkyl group, an aryl group or —O—Si($R^{b6}$)$_2$($R^{b5}$); and more preferably a hydrogen atom, an alkyl group having 1 to 4 carbon atoms, a phenyl group or —O—Si(CH$_3$)$_2$H.

$R^{b3}$ and $R^{b4}$ each are preferably a hydrogen atom, an alkyl group, an alkenyl group, an aryl group or —O—Si($R^{b8}$)$_2$($R^{b7}$); and more preferably a hydrogen atom, an alkyl group having 1 to 4 carbon atoms, a vinyl group, a phenyl group or —O—Si(CH$_3$)$_2$H.

Among these, $R^{b1}$ and $R^{b2}$ each are preferably a hydrogen atom, an alkyl group, or an aryl group; and more preferably a hydrogen atom or an alkyl group; and further preferably a hydrogen atom or a methyl group. Preferred is a combination where $R^{b1}$ is a hydrogen atom, and $R^{b2}$ is a methyl group.

$R^{b3}$ is preferably a hydrogen atom, an alkyl group, an alkenyl group, an aryl group or —O—Si($R^{b8}$)$_2$($R^{b7}$); more preferably a hydrogen atom or an alkyl group; and particularly preferably a hydrogen atom.

$R^{b4}$ is preferably a hydrogen atom, an alkyl group, an alkenyl group, an aryl group or —O—Si($R^{b8}$)$_2$($R^{b7}$); more preferably a hydrogen atom, an alkyl group or an aryl group;

furthermore preferably a hydrogen atom, a methyl group or a phenyl group; still preferably a methyl group or a phenyl group; and particularly preferably a phenyl group.

y1 is preferably an integer of 1 or more.

The sum of y1 and y2 (y1+y2) is preferably an integer of from 5 to 2,000, more preferably an integer of from 7 to 1,000, further preferably an integer of from 10 to 50, and particularly preferably an integer of from 15 to 30.

With respect to the combination of $R^{b1}$ to $R^{b3}$, it is preferable that $R^{b1}$ is a hydrogen atom or an alkyl group having 1 to 4 carbon atoms, $R^{b2}$ is an alkyl group having 1 to 4 carbon atoms, and $R^{b3}$ is a hydrogen atom; and more preferable that $R^{b1}$ is an alkyl group having 1 to 4 carbon atoms, $R^{b2}$ is an alkyl group having 1 to 4 carbon atoms, and $R^{b3}$ is a hydrogen atom.

Examples of the straight-chain structured polyorganosiloxane (B) include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %), all of which are methylhydrosiloxane-dimethylsiloxane copolymers (trimethylsiloxane terminal); HMS-991 (equivalent amount of Si—H: 67 g/mol), which is a methylhydrosiloxane polymer (trimethylsiloxane terminal), and HPM-502 (equivalent amount of Si—H: 165 g/mol), which is a methylhydrosiloxane-phenylmethylsiloxane copolymer (hydrogen terminal) (all trade names, manufactured by Gelest, Inc.).

Herein, the mole percent of MeHSiO has the same meaning as that of a value obtained by multiplying 100 by y2/(y1+y2) in the preferable combination of $R^{b1}$ to $R^{b3}$.

It is preferable for both the straight-chain structure and the branched structure not to have any vinyl group therein, from the viewpoint of suppressing a progress of the cross-linking reaction in the molecule. In particular, it is preferable for the branched structure not to have any vinyl group.

The branch-structured polyorganosiloxane (B) having at least two Si—H groups in the molecular chain thereof has a branch structure and at least two hydrosilyl groups (Si—H groups).

The specific gravity is preferably from 0.9 to 0.95.

The branch-structured polyorganosiloxane (B) is preferably represented by the following average composition formula (b).

Average composition formula (b): $[H_a(R^{b6})_{3-a}SiO_{1/2}]_{y3}[SiO_{4/2}]_{y4}$ Herein, $R^{b6}$ represents an alkyl group, a cycloalkyl group, an alkenyl group, or an aryl group; a represents 0.1 to 3, and y3 and y4 each independently represent an integer of 1 or more.

The alkyl group, the cycloalkyl group, the alkenyl group and the aryl group represented by $R^{b6}$ each have the same meaning as the alkyl group, the cycloalkyl group, the alkenyl group and the aryl group represented by any one of $R^{a2}$ and $R^{a3}$, and preferable ranges thereof are also the same.

a is preferably 1.

The content of the hydrosilyl group represented by a/3 is preferably more than 0.1 and less than 0.6, and more preferably more than 0.1 and less than 0.4.

On the other hand, when the branch-structured polyorganosiloxane (B) is represented by a chemical structure, a polyorganosiloxane in which —O—Si(CH$_3$)$_2$(H) binds to the Si atom which constitutes a main chain thereof is preferred, and one having a structure represented by the following Formula (Bb) is more preferred.

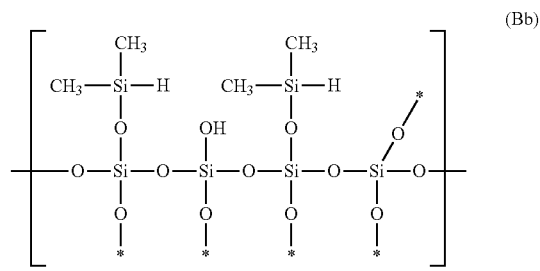

In Formula (Bb), * indicates a bond to at least the Si atom of siloxane.

Examples of the branch-structured polyorganosiloxane (B) include HQM-107 (trade name, manufactured by Gelest, Inc., HYDRIDE Q RESIN), HDP-111 (trade name, manufactured by Gelest, Inc., polyphenyl-(dimethylhydroxy)siloxane (hydrogen terminal), [(HMe$_2$SiO)(C$_6$H$_5$Si)O]: 99 to 100 mol %).

As to the polyorganosiloxane (B) having at least two Si—H groups in the molecular chain thereof used in the present invention, only one kind thereof may be used alone or at least two kinds thereof may be used in combination. Further, a straight-chain structured polyorganosiloxane (B) and a branch-structured polyorganosiloxane (B) may be used in combination.

<Silica Particles (C) Having an Average Primary Particle Size of Less than 12 nm>

The silica particles (C) having an average primary particle size of less than 12 nm used in the present invention is an ingredient which is added for the purpose of improvement in hardness and mechanical strength of a silicone resin to be obtained, particularly improvement in tear strength.

In the present invention, it is assumed that by making the average primary particle size of the silica particles (C) as small as less than 12 nm, suppression of increase in acoustic attenuation quantity and improvement of tear strength of the silicone resin have been achieved.

That is, it is assumed that a crack of the silicone resin due to a mechanical stress is suppressed by the action of fine silica particles (C) as a stopper. In particular, it is presumed that the distance among the particles becomes small due to a small average primary particle size, and therefore the particles act as a stopper more effectively whereby tear strength of the silicone resin is greatly improved.

Examples of the silica particles (C) include fumed silica, burned silica, settled silica, and a vinyl group-containing silicone resin. As to the silica particles (C), only one kind thereof may be used alone or at least two kinds thereof may be used in combination.

The average primary particle size of the silica particles (C) used in the present invention is less than 12 nm, preferably more than 3 nm and less than 12 nm, and more preferably more than 3 nm and less than 10 nm, from the viewpoint of suppressing increase in acoustic attenuation quantity of the silicone resin and improving tear strength.

The average primary particle size is described in catalogs released by silica particle manufacturers. However, that as to silica particles whose average primary particle sizes are not described in the catalogs, or newly manufactured silica particles, the average primary particle size thereof can be calculated by averaging particle sizes measured by a transmission electron microscopy (TEM). Specifically, with respect to one of particles photographed by TEM, a minor axis and a major axis thereof are measured and an average of these lengths is calculated as a particle size of the one particle. In the present specification, particle sizes of at least 300 particles are averaged and the obtained value is defined as an average primary particle size.

Further, in a case where the silica particles (C) has been subjected to the surface treatment described below, the average primary particle size means an average primary particle size of surface-treated silica particles (C).

As to the silica particles (C) used in the present invention, from the viewpoint of improving hardness and mechanical strength of the silicone resin to be obtained, the specific surface area thereof is preferably from 50 to 400 m$^2$/g, and more preferably from 100 to 400 m$^2$/g.

As to the silica particles (C) used in the present invention, silica particles whose surface has been subjected to a surface treatment are preferred. Silica particles, processed with a saturated aliphatic acid or silane as a surface treatment, are preferred. In particular, silica particles processed with silane are preferred.

As for the silane treatment, a silica particle surface is preferably treated with a silane coupling agent. In particular, from the viewpoint of improving hardness and mechanical strength of the silicone resin, a silane coupling agent having a hydrolysable group is preferred. The hydrolysable group in the silane coupling agent is hydrolyzed by water to form a hydroxyl group, and this hydroxyl group brings into a dehydration condensation reaction with a hydroxyl group on the surface of the silica particles whereby a surface reforming of the silica particles is performed, so that hardness and mechanical strength of the silicone resin to be obtained can be improved. Examples of the hydrolysable group include an alkoxy group, an acyloxy group, and a halogen atom.

It is preferred that the surface of the silica particle is surface-reformed so as to become hydrophobic, because affinity of the silica particles (C) for the polyorganosiloxane (A) and the polyorganosiloxane (B) is improved whereby hardness and mechanical strength of the silicone resin to be obtained are improved.

Examples of the silane coupling agent having a hydrophobic group as a functional group include: an alkoxysilane such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane; chlorosilanes such as methyltrichlorosilane, dimethyldichlorosilane (DDS), trimethylchlorosilane, and phenyltrichlorosilane; and hexamethyldisilazane (HMDS).

Examples of the silane coupling agent having a vinyl group as a functional group include: an alkoxysilane such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

As to the silica particles (C) used in the present invention, silica particles whose surface has been treated with a silane compound are preferred. Silica particles treated with a trialkylsilylation agent are more preferred. Silica particles treated with a trimethylsilylation agent are still more preferred.

Examples of the silane compound include the above silane coupling agents and silane coupling agents whose functional group is substituted with an alkyl group.

Examples of the trialkylsilylation agent include: trimethylchlorosilane and hexamethyldisilazane (HMDS) described as examples of the above silane coupling agents; trimethylmethoxysilane which is a silane coupling agent whose functional group is substituted with an alkyl group.

Examples of a commercially available silane coupling agent include hexamethyldisilazane (HMDS) (trade name: HEXAMETHYLDISILAZANE (SIH6110.1), manufactured by Gelest, Inc.).

The silanol group (Si—OH group) which is present on the surface of the silica particles reacts with hexamethyldisilazane (HMDS), and the surface of the silanol group is covered with a trimethylsilyl group whereby the surface of the silica particles is reformed to a hydrophobic property.

Examples of commercially available silica particles (C) include: AEROSIL (registered trademark) R812 (average primary particle size 7 nm, HMDS surface treated), AEROSIL (registered trademark) R812S (average primary particle size 7 nm, HMDS surface treated), AEROSIL (registered trademark) RX300 (average primary particle size 7 nm, HMDS surface treated), AEROSIL (registered trademark) RX380S (average primary particle size 5 nm, HMDS surface treated), AEROSIL (registered trademark) R976S (average primary particle size 7 nm, DDS surface treated), all of which are a hydrophobic fumed silica manufactured by Nippon Aerosil Co., Ltd.; and AEROSIL (registered trademark) 300 (average primary particle size 7 nm), AEROSIL (registered trademark) 300CF (average primary particle size 7 nm), AEROSIL (registered trademark) 380 (average primary particle size 7 nm), all of which are a hydrophilic fumed silica manufactured by Nippon Aerosil Co., Ltd.

Ordinarily, the vinyl group which the polyorganosiloxane (A) has and the Si—H group which the polyorganosiloxane (B) has stoichiometrically react in a proportion of 1:1.

However, in the present invention, the average primary particle size of the silica particles (C) is so small that the silica particles (C) are densely packed in the spaces between the polyorganosiloxane (A) and the polyorganosiloxane (B), and therefore molecular chain movement of the polyorganosiloxane (A) and the polyorganosiloxane (B) is restricted.

As a result, in order that all vinyl groups react with the Si—H groups, an equivalent amount of the Si—H group, which the polyorganosiloxane (B) has, with respect to the vinyl group, which the polyorganosiloxane (A) has, i.e. vinyl group: Si—H group is preferably from 1:1.1 to 1:8, and more preferably from 1:1.2 to 1:5.

<Other Ingredient>

In addition to the polyorganosiloxane (A) having a vinyl group, the polyorganosiloxane (B) having at least two Si—H groups in the molecular chain thereof and the silica particles (C) having an average primary particle size of less than 12 nm, the composition for the acoustic-wave probe of the present invention may appropriately contain a platinum catalyst for addition polymerization reaction, a curing retardant, a solvent, a dispersant, a pigment, a dye, an antistatic agent, an antioxidant, a flame retardant, a thermal conductivity improver, and the like.

—Catalyst—

Examples of the catalyst include platinum and a platinum-containing compound (hereinafter, also referred to as platinum compound). As for the platinum and the platinum compound, arbitrary materials may be used.

Specific examples thereof include platinum black, platinum carried on silica, carbon black, or the like, platinic chloride or an alcohol solution of platinic chloride, a complex salt of platinic chloride and olefin, a complex salt of platinic chloride and vinylsiloxane, and the like. As to the catalyst, only one kind thereof may be used solely, or at least two kinds thereof may be used in combination.

The content of the catalyst can be appropriately determined within a catalytic amount.

The catalyst is required in the hydrosilylation reaction in which the Si—H group of the polyorganosiloxane (B) adds to the vinyl group of the polyorganosiloxane (A). The polyorganosiloxane (A) is cross-linked with the polyorganosiloxane (B) by addition-curing reaction due to hydrosilylation whereby a silicone resin is formed.

Herein, the catalyst may be contained in the composition for an acoustic-wave probe of the present invention. Alternatively, the catalyst may be brought into contact with the composition for an acoustic-wave probe without containing it in the composition for the acoustic-wave probe. Of these, the latter is preferable.

Examples of a commercially available platinum catalyst include a platinum compound (trade name: PLATINUM CYCLOVINYLMETHYLSILOXANE COMPLEX IN CYCLIC METHYLVINYLSILOXANES (SIP6832.2), Pt concentration: 2 mass %, manufactured by Gelest, Inc.).

In a case where the composition for an acoustic-wave probe of the present invention contains a catalyst, the content of the catalyst is, from the viewpoint of reactivity, preferably from 0.00001 to 0.05 part by mass, more preferably from 0.00001 to 0.01 part by mass, still more preferably from 0.00002 to 0.01 part by mass, and particularly preferably from 0.00005 to 0.005 part by mass to 100 parts by mass of the polysiloxane mixture.

Further, a temperature for curing may be adjusted by selecting an appropriate platinum catalyst. For example, platinum-vinyldisiloxane is used for room temperature curing (RTV) at 50° C. or less, while platinum-cyclic vinylsiloxane is used for high temperature curing (HTV) at 130° C. or more.

—Curing Retardant—

The curing retardant for curing reaction is used according to the necessity. The curing retardant is used for the intended purpose of retarding addition-curing reaction in the presence of a platinum catalyst. Examples thereof include a low molecular weight vinylmethylsiloxane homopolymer (trade name: VMS-005, manufactured by Gelest, Inc.).

The curing speed, that is, working hours may be adjusted by the content of the curing retardant.

<Production Method of Composition for Acoustic-wave Probe and Silicone Resin for Acoustic-wave Probe>

The composition for the acoustic-wave probe of the present invention can be prepared by an arbitrary method.

For example, the composition for the acoustic-wave probe can be obtained by kneading its ingredients by means of kneader, pressure kneader, Banbury mixer (continuous kneader), or a double roll-kneading machine. There is no particular limitation to the addition order of each ingredient.

From the viewpoint of obtaining a homogeneous composition, firstly, it is preferable that the silica particles (C) having an average primary particle size of less than 12 nm are dispersed in both the polyorganosiloxane (A) having a vinyl group and the polyorganosiloxane (B) having at least two Si—H groups in the molecular chain thereof thereby to make a polyorganosiloxane mixture. After that, a catalyst is added to the polyorganosiloxane mixture in which the silica particles (C) has been dispersed, and then by degassing under reduced pressure, the composition for an acoustic-wave probe can be prepared.

By curing the thus-obtained composition for an acoustic-wave probe of the present invention, the silicone resin for an acoustic-wave probe of the present invention can be obtained. Specifically, for example, by heating and curing the composition at 20 to 200° C. for 5 to 500 minutes, the silicone resin for an acoustic-wave probe can be obtained.

<Mechanical Strength and Acoustic Characteristic of Silicone Resin>

Hereinafter, a detailed description is given about mechanical strength and acoustic characteristics of the silicone resin.

Herein, the acoustic characteristics are described about ultrasonic characteristics. However, the acoustic characteristics are not limited to ultrasonic characteristics, but are related to acoustic characteristics having appropriate frequencies which are selected depending on a target to be examined, measuring conditions, and the like.

[Hardness]

With respect to a 2 mm-thick silicone resin sheet, type-A durometer hardness is measured using a rubber hardness tester (for example, RH-201A, trade name, manufactured by EXCEL INC.) in accordance with JIS K6253-3 (2012).

The hardness is preferably at least 20, and more preferably at least 30. The upper limit is practically 80 or less. It is preferable that the hardness being within the above range, the silicone resin for an acoustic-wave probe is prevented from deforming when it is incorporated into and used as a part of an acoustic-wave probe.

[Tensile Test]

With respect to a 1 mm-thick silicone resin sheet, tensile strength at break and tensile elongation at break are measured in accordance with JIS K6251 (2010).

The tensile strength at break is preferably 2.0 MPa or more, and the tensile elongation at break is preferably 300% or more. The upper limit is practically 10 MPa or less in terms of tensile strength at break, and practically 1,500% or less in terms of tensile elongation at break.

[Test of Tear Strength]

With respect to a 2 mm-thick silicone resin sheet, a trouser-type specimen is prepared and tear strength thereof is measured in accordance with JIS K6252 (2007).

The tear strength is preferably 20 N/cm or more, and more preferably 30 N/cm or more. The upper limit is practically 100 N/cm or less.

[Williams Abrasion Test]

A silicone resin sheet having a size of length: 20 mm×width: 20 mm×thickness: 10 mm is subjected to a test according to JIS K6264-2 by using an apparatus for Williams Abrasion Test, thereby the mass of the silicone resin sheet before the test and the mass of the silicone resin sheet after the test are weighed. A reduction proportion (%) of the mass calculated by the following formula is evaluated as Williams abrasion amount (%).

("Mass of silicone resin sheet before test"−"mass of silicone resin sheet after test")/"Mass of silicone resin sheet before test"×100

Williams abrasion amount is preferably 1% or less, more preferably 0.7% or less, furthermore preferably 0.5% or less, and the smaller Williams abrasion amount is, the more preferable it is.

[Acoustic Impedance]

With respect to a 2 mm-thick silicone resin sheet, a density at 25° C. is measured using an electronic densitometer (for example, "SD-200L", trade name, manufactured by Alfa Mirage Co., Ltd.) in accordance with a density measuring method of A method (a method of collecting gas over water) described in JIS-K7112 02 (1999). The sonic speed of the acoustic wave is measured at 25° C. using a sing-around type sonic speed measuring apparatus (for example, "UVM- 2-model", trade name, manufactured by ULTRASONIC ENGINEERING CO., LTD.) in accordance with JIS Z2353-2003.

Acoustic impedance is calculated from a product of the measured density and sonic speed.

[Acoustic (Ultrasonic) Attenuation Quantity and Sensitivity]

Sine wave signal of 5 MHz (1 wave) generated by an ultrasonic oscillator (for example, function generator "FG-350", trade name, manufactured by IWATSU TEST INSTRUMENT CORPORATION) is input into an ultrasonic probe (for example, manufactured by Japan Probe Corporation) and a pulse wave having a center frequency of 5 MHz from the ultrasonic probe is generated in water. Magnitude scales of amplitudes before and after the generated ultrasonic wave passes through a 2 mm-thick silicone resin sheet are measured under the condition of water temperature of 25° C. using an ultrasonic receiver (for example, oscilloscope "VP-5204A", trade name, manufactured by Panasonic Corporation), and by comparing acoustic (ultrasonic) sensitivities, acoustic (ultrasonic) attenuation quantity of each sheet is compared with one another.

The acoustic (ultrasonic) sensitivity is a value obtained from the following calculating formula.

In the following calculating formula, Vin represents a voltage peak value of the input wave, having a half width of 50 nsec or less by an ultrasonic oscillator. Vs represents a voltage value obtained when, after a generated acoustic wave (ultrasonic wave) has passed through a sheet, the ultrasonic oscillator receives the acoustic wave (ultrasonic wave) which reflects from the other side of the sheet.

$$\text{Acoustic (ultrasonic) sensitivity}=20\times\text{Log}(Vs/Vin)$$

In the evaluation system in the present invention, the acoustic (ultrasonic) sensitivity is preferably −72 dB or more, and more preferably −71 dB or more.

The composition for an acoustic-wave probe of the present invention is useful as a member of medical device, and for example, can be preferably used for an acoustic-wave probe and a device for measuring an acoustic wave. The device for measuring an acoustic wave of the present invention is not limited to an ultrasonic diagnosis device or a device for measuring a photo acoustic wave, but means a device which receives an acoustic wave reflected on or generated from a target and displays thereon the target as an image or signal intensities.

In particular, for example, the composition for an acoustic-wave probe of the present invention can be used for: an acoustic lens of the ultrasonic diagnosis device; a material of an ultrasonic matching layer which is located between a piezoelectric element and an acoustic lens and has a role to match an acoustic impedance between the piezoelectric element and the acoustic lens; a material of an acoustic lens in a device for measuring a photo acoustic wave and in an ultrasonic endoscope; and a material of an acoustic lens in an ultrasonic probe provided with capacitive micromachined ultrasonic transducers (cMUT) as an ultrasonic transducer array.

The silicone resin for an acoustic-wave probe of the present invention can be preferably used, specifically for example, for ultrasonic diagnosis devices described in JP-A-2005-253751, JP-A-2003-169802 and the like, and devices for measuring an acoustic wave such as devices for measuring a photo acoustic wave described in JP-A-2013-202050, JP-A-2013-188465, JP-A-2013-180330, JP-A-2013-158435, JP-A-2013-154139 and the like.

<<Search Unit (Probe) for an Acoustic Wave>>

Hereinafter, more detailed explanation is given about a configuration of the acoustic-wave probe of the present invention, on the basis of the configuration of the ultrasonic probe in the ultrasonic diagnosis device, shown in FIG. 1. The ultrasonic probe is a probe which particularly uses an ultrasonic wave as an acoustic wave of an acoustic-wave probe. Therefore, a basic structure of the ultrasonic probe may be applied to an acoustic-wave probe without any change.

—Ultrasonic Probe—

Ultrasonic probe 10 is a major structural component of the ultrasonic diagnosis device and has a function of not only generating an ultrasonic wave but also transmitting and receiving an ultrasonic beam. As to the constitution of the ultrasonic probe 10, as shown in FIG. 1, acoustic lens 1, acoustic matching layer 2, piezoelectric element layer 3 and backing material 4 are disposed in this order from the tip (the side which contacts with a living body which is a target to be examined) portion. Recently, for the purpose of receiving higher-order harmonic, an ultrasonic probe having a laminate structure which is composed of an ultrasonic oscillator for transmission (piezoelectric element) and in an ultrasonic oscillator for reception (piezoelectric element), whose materials are different from one another, has also been proposed.

<Piezoelectric Element Layer>

Piezo element layer 3 is a portion of generating an ultrasonic wave. Electrodes are attached to both sides of the piezoelectric element, and when a voltage is applied, the piezoelectric element vibrates by repeating contraction and expansion thereby generating an ultrasonic wave.

As to the materials which constitute the piezoelectric element, the following materials are widely used: a single crystal such as quartz crystal, $LiNbO_3$, $LiTaO_3$, and $KNbO_3$; a thin film of ZnO, MN and the like; and a so-called ceramics inorganic piezoelectric body in which a $Pb(Zr,Ti)O_3$-based sintered body and the like has been subjected to a polarization treatment. Commonly, piezoelectric ceramics such as PZT: lead zirconate titanate and the like, which has high conversion efficiency are used.

Further, as to the piezoelectric element which detects a receiving wave on the high frequency side, broader bandwidth sensitivity is required. Therefore, as a piezoelectric element which is suitable for high frequency and broadband, an organic piezoelectric body using an organic macromolecular substance such as polyvinylidene fluoride (PVDF) or the like is used.

Further, JP-A-2011-071842 and the like disclose cMUT using a MEMS (Micro Electro Mechanical Systems) technique, by which an alley structure, exhibiting excellent short pulse characteristics and broadband characteristics and having excellent productivity with less dispersion in characteristics, can be obtained.

In the present invention, any of the piezoelectric element materials may be preferably used.

<Backing Material>

Backing material 4 is disposed on a backside of the piezoelectric element layer 3. By suppressing a superfluous vibration, the pulse width of the ultrasonic wave is shortened, which contributes to improvement in range resolution of an ultrasonic diagnosis image.

<Acoustic Matching Layer>

Acoustic matching layer 2 is disposed in order to reduce a difference in acoustic impedance between the piezoelectric element layer 3 and a target to be examined, thereby efficiently transmitting and receiving an ultrasonic wave.

The composition for an ultrasonic probe of the present invention can be preferably used as a material of the acoustic matching layer, since a difference between a biogenic acoustic impedance (1.4 to $1.7 \times 10^6$ kg/m$^2$·sec) and the above composition is small. The acoustic matching layer in the present invention preferably contains 10 mass % or more of a silicone resin for an acoustic-wave probe obtained by curing the composition for an ultrasonic probe of the present invention.

<Acoustic Lens>

Acoustic lens 1 is disposed in order to focus an ultrasonic wave to the slice direction through the use of refraction, thereby improving resolution. Further, the acoustic lens is required to adhere firmly to a living body, which is a target to be examined, thereby making an ultrasonic wave consistent with a biogenic acoustic impedance (1.4 to $1.7 \times 10^6$ kg/m$^2$·sec in human body), and it is required that the ultrasonic attenuation quantity of the acoustic lens 1 itself is small.

That is, as for the material of the acoustic lens 1, if the sonic speed thereof is adequately smaller than the sonic speed of human body and the ultrasonic attenuation is small and the acoustic impedance thereof is close to a value of human body's skin, the ultrasonic transmission and reception sensitivity is improved.

The composition for an acoustic-wave probe (being a composition for an ultrasonic probe) of the present invention can be also preferably used as an acoustic lens material.

Explanation is given about the behavior of the ultrasonic probe 10 having the foregoing constitution. Piezoelectric element layer 3 is resonated by applying a voltage to electrodes disposed on both sides of the piezoelectric element and the generated ultrasonic signals are transmitted from an acoustic lens to a target to be examined. At the time of reception, the piezoelectric element layer 3 is vibrated by reflected signals (echo signals) from the target to be examined and the generated vibration is electrically converted to signals, thereby obtaining an image.

In particular, in a case where the acoustic lens obtained from the composition for an ultrasonic probe of the present invention is used in a commonly-used medical ultrasonic transducer, a conspicuous improvement effect of sensitivity can be confirmed at approximately 5 MHz or more of ultrasonic transmit frequencies. In particular, a particularly conspicuous improvement effect of sensitivity can be expected at 10 MHz or more of ultrasonic transmit frequencies.

Hereinafter, a detailed description is given that a device, into which the acoustic lens obtained from the composition for an ultrasonic probe of the present invention is incorporated, particularly achieves a function with respect to the previous problems.

For devices other than the following devices, the composition for an ultrasonic probe of the present invention generates excellent effects.

—Ultrasonic Probe Provided with cMUT (Capacitive Micromachined Ultrasonic Transducers)—

In case where cMUT devices described in JP-A-2006-157320, JP-A-2011-71842, and the like are used for a transducer alley for ultrasonic diagnosis, usually, sensitivity thereof becomes lower compared to a transducer using a commonly-used piezoelectric ceramics (PZT).

By using the acoustic lens obtained from the composition for an acoustic-wave probe of the present invention, however, sensitivity insufficiency of the cMUT can be compensated. This compensation enables sensitivity of the cMUT to approximate performance of conventional transducers.

The cMUT device is prepared by a MEMS technique whereby an ultrasonic probe having higher mass-production property with a lower cost compared to piezoelectric ceramics probe can be placed on the market.

—Device for Measuring Photo Acoustic Wave by Photo Ultrasonic Imaging—

In the photo ultrasonic imaging (PAI: Photo Acoustic Imaging) described in JP-A-2013-158435 and the like, an image is displayed by imaging of the ultrasonic wave which is generated at the time when the inside of the human body is irradiated by a light (electromagnetic wave) and then a human tissue is adiabatically expanded by the irradiated light, or alternatively signal intensities of the generated ultrasonic wave are displayed.

Herein, a sound pressure of the ultrasonic wave generated by the light irradiation is so small amount that this causes a problem of difficulty to observe a deep part of the human body.

However, by using the acoustic lens obtained from the composition for an acoustic-wave probe of the present invention, effects on the above problem can be exhibited.

—Ultrasonic Endoscope—

As to the ultrasonic wave in the ultrasonic endoscope described in JP-A-2008-311700 and the like, a signal wire cable is longer due to its structure compared to a transducer for a body surface, and as a result, improvement in sensitivity of the transducer against a cable loss is a task. As regards this task, however, it is said that there is no effective means for improvement in sensitivity for the reasons set forth below.

Firstly, in the ultrasonic diagnosis device for a body surface, it is possible to install an amplifier circuit, an AD conversion IC, and the like at the tip of the transducer. In contrast, for the reason that the ultrasonic endoscope is used by inserting it into the inside of the body, space for the transducer is small, so that it is difficult to install the amplifier circuit, the AD conversion IC, and the like at the tip of the transducer.

Secondly, in terms of physical properties and process aptitude, it is difficult to apply piezoelectric single crystal, which is adopted in a transducer of the ultrasonic diagnosis device for a body surface, to a transducer having transmit frequency of the ultrasonic wave in the range from 7 to 8 MHz or greater. Further, for the reason that the ultrasonic transducer for an endoscope is generally a probe having transmit frequency of the ultrasonic wave in the range from 7 to 8 MHz or greater, improvement in sensitivity by use of a piezoelectric single crystal material is difficult.

However, by using the acoustic lens obtained from the composition for an acoustic-wave probe of the present invention, sensitivity of the ultrasonic transducer for an endoscope can be improved.

Further, even if the same transmit frequency (for example, 10 MHz) of the ultrasonic wave, effectiveness is exhibited particularly in the case of using the acoustic lens obtained from the composition for an acoustic-wave probe of the present invention in the ultrasonic transducer for an endoscope.

The present invention will be described in more detail based on the following examples, but the invention is not intended to be limited thereto.

EXAMPLES

Hereinafter, the present invention is explained in more detail on the basis of Examples in which an ultrasonic wave is used as an acoustic wave. The present invention is not limited to the ultrasonic wave, but an ultrasonic wave having an audio frequency may be used, as long as an adequate frequency is selected in accordance with a target to be examined, measurement conditions, and the like.

Example 1

79.6 parts by mass of a vinyl-terminated polydimethylsiloxane ("DMS-V42", trade name, manufactured by Gelest, Inc., mass average molecular weight: 72,000), 2.4 parts by mass of a methylhydrosiloxane-dimethylsiloxane copolymer ("HMS-301", trade name, manufactured by Gelest, Inc., mass average molecular weight: 2,000, proportion of methylhydrosiloxane: 27 mol %), and 18 parts by mass of a fumed silica ("AEROSIL RX300", trade name, manufactured by NIPPON AEROSIL CO., LTD., average primary particle size: 7 nm, hexamethyldisilazane (HMDS) surface treated) were kneaded for 2 hours using a kneader to prepare a homogeneous paste. To this paste, 500 ppm of a platinum catalyst solution ("SIP6821.3", trade name, manufactured by Gelest, Inc.) was added and mixed, and then was degassed under reduced pressure. Then, the degassed mixture was placed in a metal mold of 150 mm×150 mm and was subjected to a thermal treatment at 60° C. for 3 hours. Thus, silicone resin sheets having a thickness of 1 mm and 2 mm respectively were obtained.

Examples 2 to 18 and Comparative Examples 1 to 3

Predetermined silicone resin sheets were obtained except that the ingredients and composition of the polysiloxane mixture of Example 1 were changed as shown in the following Tables 1 to 3.

<Evaluations of Mechanical Strength and Ultrasonic Characteristics>

With respect to the silicone resin sheets of Examples 1 to 18 and Comparative Examples 1 to 3, the following evaluations were carried out.

[Hardness]

With respect to the obtained silicone resin sheet having a thickness of 2 mm, type-A durometer hardness was measured using a rubber hardness tester ("RH-201A", trade name, manufactured by EXCELINC.) in accordance with JIS K6253-3 (2012).

[Tensile Test]

With respect to the obtained silicone resin sheet having a thickness of 1 mm, tensile strength at break and tensile elongation at break were measured in accordance with JIS K6251.

[Test of Tear Strength]

With respect to the obtained silicone resin sheet having a thickness of 2 mm, a trouser-type specimen was prepared, and tear strength thereof was measured in accordance with JIS K6252 (2007).

[Williams Abrasion Test]

In Examples 1 to 18 and Comparative Examples 1 to 3, specimens having a size of length: 20 mm×width: 20 mm×height: 10 mm were similarly prepared. The obtained specimen was subjected to a test according to JIS K6264-2 by using an apparatus (No. 275) for Williams Abrasion Test manufactured by YASUDA SEIKI SEISAKUSHO, LTD., thereby the mass of the specimen before the test and the mass of the specimen after the test were weighed and a reduction proportion (%) of the mass was calculated by the following formula. In Tables 1 to 3 below, the reduction proportion (%) of the mass calculated by the following formula was described as Williams abrasion amount (%).

("Mass of silicone resin sheet before test"–"mass of silicone resin sheet after test")/"Mass of silicone resin sheet before test"×100

[Acoustic Impedance]

With respect to the obtained silicone resin sheet having a thickness of 2 mm, the density at 25° C. was measured using an electronic densitometer ("SD-200L", trade name, manufactured by Alfa Mirage Co., Ltd.) in accordance with a density measuring method of A method (a method of collecting gas over water) described in JIS-K7112 (1999). The sonic speed of the ultrasonic wave was measured at 25° C. using a sing-around type sonic speed measuring apparatus ("UVM-2-model", trade name, manufactured by ULTRASONIC ENGINEERING CO., LTD.) in accordance with JIS Z2353 (2003). Acoustic impedance was obtained by multiplying the measured density by sonic speed.

[Acoustic (Ultrasonic) Sensitivity]

Sine wave signal of 5 MHz (1 wave) generated by an ultrasonic oscillator (function generator "FG-350", trade name, manufactured by IWATSU TEST INSTRUMENT CORPORATION) was input into an ultrasonic probe (manufactured by Japan Probe Corporation) and a pulse wave having a center frequency of 5 MHz was generated from the ultrasonic probe in water. Magnitude scales of amplitudes before and after the generated ultrasonic wave passed through the obtained 2 mm-thick silicone resin sheet were measured under the condition of water temperature of 25° C. using an ultrasonic receiver (oscilloscope "VP-5204A", trade name, manufactured by Panasonic Corporation), and by comparing acoustic (ultrasonic) sensitivities, acoustic (ultrasonic) attenuation quantity of each sheet was compared with one another.

The acoustic (ultrasonic) sensitivity is a value obtained from the following calculating formula.

In the following calculating formula, Vin represents a voltage peak value of the input wave having a half width of 50 nsec or less by an ultrasonic oscillator. Vs represents a voltage value obtained when, after a generated acoustic wave (ultrasonic wave) has passed through a sheet, the ultrasonic oscillator receives the acoustic wave (ultrasonic wave) which reflects from the other side of the sheet.

Acoustic (ultrasonic) sensitivity=$20 \times \mathrm{Log}(Vs/Vin)$

The obtained results are shown together in the following Tables 1 to 3.

In Tables 1 to 3, the mass average molecular weight of the polyorganosiloxanes (A) and (B) is described simply as "molecular weight". Further, the kind of each material is described by its trade name.

TABLE 1

| | | Item | Ex 1 | Ex 2 | Ex 3 | Ex 4 | Ex 5 | Ex 6 | Ex 7 | Ex 8 | Ex 9 |
|---|---|---|---|---|---|---|---|---|---|---|---|
| Composition of mixture | Silica particles (C) | Kind | RX300 | R976S | 300 | RX380S | H 20 | RX300 | RX300 | RX300 | RX300 |
| | | Average primary particle size [nm] | 7 | 7 | 7 | 5 | 10 | 7 | 7 | 7 | 7 |
| | | Surface treatment | HMDS | DDS | — | HMDS | HMDS | HMDS | HMDS | HMDS | HMDS |

TABLE 1-continued

| | | Item | Ex 1 | Ex 2 | Ex 3 | Ex 4 | Ex 5 | Ex 6 | Ex 7 | Ex 8 | Ex 9 |
|---|---|---|---|---|---|---|---|---|---|---|---|
| | | Amount [mass %] | 18.0 | 18.0 | 18.0 | 18.0 | 18.0 | 18.0 | 18.0 | 18.0 | 18.0 |
| Poly-siloxane | Component (A) | Kind | DMS-V42 | DMS-V42 | DMS-V42 | DMS-V42 | DMS-V42 | DMS-V31 | DMS-V35 | DMS-V46 | DMS-V52 |
| | | Molecular weight | 72,000 | 72,000 | 72,000 | 72,000 | 72,000 | 28,000 | 49,500 | 117,000 | 155,000 |
| | | Amount [mass %] | 79.6 | 79.6 | 79.6 | 79.6 | 79.6 | 79.6 | 79.6 | 79.6 | 79.6 |
| | Component (B) | Kind | HMS-301 | HMS-301 | HMS-301 | HMS-301 | HMS-301 | HMS-301 | HMS-301 | HMS-301 | HMS-301 |
| | | Molecular weight | 2,000 | 2,000 | 2,000 | 2,000 | 2,000 | 2,000 | 2,000 | 2,000 | 2,000 |
| | | Amount [mass %] | 2.4 | 2.4 | 2.4 | 2.4 | 2.4 | 2.4 | 2.4 | 2.4 | 2.4 |
| Evaluation | JIS Hardness | | 31 | 34 | 37 | 27 | 33 | 40 | 36 | 26 | 23 |
| | Tensile strength at break [MPa] | | 2.1 | 2.7 | 2.8 | 2.5 | 1.9 | 2.8 | 2.5 | 1.7 | 1.4 |
| | Tensile elongation at break [%] | | 880 | 810 | 650 | 930 | 530 | 640 | 1050 | 780 | 710 |
| | Tear strength [N/cm] | | 26 | 24 | 18 | 32 | 13 | 12 | 19 | 29 | 33 |
| | Williams abrasion amount [%] | | 0.36 | 0.37 | 0.45 | 0.33 | 0.42 | 0.41 | 0.39 | 0.36 | 0.35 |
| | Acoustic impedance [$\times 10^6$ kg/m$^2$/s] | | 1.04 | 1.04 | 1.05 | 1.04 | 1.04 | 1.04 | 1.04 | 1.04 | 1.04 |
| | Acoustic (ultrasonic) sensitivity [dB] | | −70.2 | −70.8 | −71.6 | −69.0 | −71.1 | −69.6 | −69.8 | −70.4 | −70.6 |

"Ex" means Example according to the present invention.

TABLE 2

(Table 1-continued)

| | | Item | Ex 10 | Ex 11 | Ex 12 | Ex 13 | Ex 14 | Ex 15 | Ex 16 | Ex 17 | Ex 18 |
|---|---|---|---|---|---|---|---|---|---|---|---|
| Composition of mixture | Silica particles (C) | Kind | RX300 | RX300 | RX300 | RX300 | RX300 | RX300 | RX300 | RX300 | RX300 |
| | | Average primary particle size [nm] | 7 | 7 | 7 | 7 | 7 | 7 | 7 | 7 | 7 |
| | | Surface treatment | HMDS | HMDS | HMDS | HMDS | HMDS | HMDS | HMDS | HMDS | HMDS |
| | | Amount [mass %] | 18.0 | 12.0 | 24.0 | 20.0 | 20.0 | 24.0 | 24.0 | 24.0 | 24.0 |
| | Polysiloxane Component (A) | Kind | DMS-V42 | DMS-V42 | DMS-V42 | PDV-0535 | PDV-0541 | PDV-1631 | PDV-1635 | PDV-1641 | PDV-1635 |
| | | Molecular weight | 72,000 | 72,000 | 72,000 | 47,500 | 60,000 | 19,000 | 35,300 | 55,000 | 35,300 |
| | | Amount [mass %] | 71.0 | 85.4 | 73.7 | 77.8 | 78.2 | 70.0 | 72.7 | 73.8 | 74.6 |
| | Component (B) | Kind | HMS-064 | HMS-301 | HMS-301 | HMS-501 | HMS-501 | HPM-502 | HPM-502 | HPM-502 | HMS-991 |
| | | Molecular weight | 60,000 | 2,000 | 2,000 | 1,100 | 1,100 | 4,500 | 4,500 | 4,500 | 1,600 |
| | | Amount [mass %] | 11.0 | 2.6 | 2.3 | 2.2 | 1.8 | 6.0 | 3.3 | 2.2 | 1.4 |
| Evaluation | JIS Hardness | | 27 | 26 | 36 | 35 | 30 | 41 | 35 | 25 | 40 |
| | Tensile strength at break [MPa] | | 1.7 | 1.6 | 2.7 | 2.5 | 2.2 | 2.9 | 2.3 | 1.5 | 2.7 |
| | Tensile elongation at break [%] | | 950 | 560 | 730 | 420 | 630 | 280 | 330 | 460 | 300 |
| | Tear strength [N/cm] | | 24 | 11 | 31 | 16 | 22 | 10 | 17 | 21 | 11 |
| | Williams abrasion amount [%] | | 0.36 | 0.44 | 0.34 | 0.44 | 0.41 | 0.46 | 0.44 | 0.41 | 0.42 |
| | Acoustic impedance [$\times 10^6$ kg/m$^2$/s] | | 1.04 | 1.02 | 1.06 | 1.18 | 1.18 | 1.42 | 1.42 | 1.42 | 1.41 |
| | Acoustic (ultrasonic) sensitivity [dB] | | −70.4 | −69.0 | −71.6 | −71.0 | −70.7 | −72.3 | −72.0 | −71.8 | −72.3 |

"Ex" means Example according to the present invention.

TABLE 3

(Table 1-continued)

| | | Item | C Ex 1 | C Ex 2 | C Ex 3 |
|---|---|---|---|---|---|
| Composition of mixture | Silica particles (C) | Kind | RX200 | — | 200 |
| | | Average primary particle size [nm] | 12 | — | 12 |
| | | Surface treatment | HMDS | — | — |
| | | Amount [mass %] | 18.0 | 0.0 | 18.0 |
| | Polysiloxane Component (A) | Kind | DMS-V42 | DMS-V42 | DMS-V42 |
| | | Molecular weight | 72,000 | 72,000 | 72,000 |
| | | Amount [mass %] | 79.6 | 97.0 | 79.6 |
| | Component (B) | Kind | HMS-301 | HMS-301 | HMS-301 |
| | | Molecular weight | 2,000 | 2,000 | 2,000 |
| | | Amount [mass %] | 2.4 | 3.0 | 2.4 |

TABLE 3-continued (Table 1-continued)

| | Item | C Ex 1 | C Ex 2 | C Ex 3 |
|---|---|---|---|---|
| Evaluation | JIS Hardness | 37 | 11 | 41 |
| | Tensile strength at break [MPa] | 1.7 | 0.3 | 2.0 |
| | Tensile elongation at break [%] | 310 | 460 | 270 |
| | Tear strength [N/cm] | 8 | 1 | 6 |
| | Williams abrasion amount [%] | 0.72 | 3.30 | 0.82 |
| | Acoustic impedance [×10$^6$ kg/m$^2$/s] | 1.04 | 1.00 | 1.05 |
| | Acoustic (ultrasonic) sensitivity [dB] | −72.4 | −62.8 | −70.0 |

"C Ex" means Comparative Example.

<Notes in Tables>
[Polyorganosiloxane Component (A)]
DMS (trade name) series and PDV (trade name) series manufactured by Gelest, Inc.
  DMS-V31: trade name, vinyl-terminated polydimethylsiloxane, mass average molecular weight: 28,000
  DMS-V35: trade name, vinyl-terminated polydimethylsiloxane, mass average molecular weight: 49,500
  DMS-V42: trade name, vinyl-terminated polydimethylsiloxane, mass average molecular weight: 72,000
  DMS-V46: trade name, vinyl-terminated polydimethylsiloxane, mass average molecular weight: 117,000
  DMS-V52: trade name, vinyl-terminated polydimethylsiloxane, mass average molecular weight: 155,000
  PDV-0541: trade name, vinyl-terminated diphenylsiloxane-dimethylsiloxane copolymer, mass average molecular weight: 60,000, proportion of diphenylosiloxane: 5 mol %
  PDV-0535: trade name, vinyl-terminated diphenylsiloxane-dimethylsiloxane copolymer, mass average molecular weight: 47,500, proportion of diphenylosiloxane: 5 mol %
  PDV-1641: trade name, vinyl-terminated diphenylsiloxane-dimethylsiloxane copolymer, mass average molecular weight: 55,000, proportion of diphenylosiloxane: 16 mol %
  PDV-1635: trade name, vinyl-terminated diphenylsiloxane-dimethylsiloxane copolymer, mass average molecular weight: 35,300, proportion of diphenylosiloxane: 16 mol %
  PDV-1631: trade name, vinyl-terminated diphenylsiloxane-dimethylsiloxane copolymer, mass average molecular weight: 19,000, proportion of diphenylosiloxane: 16 mol %
[Polyorganosiloxane Component (B)]
HMS (trade name) series and HPM (trade name) series manufactured by Gelest, Inc.
  HMS-064: trade name, methylhydrosiloxane-dimethylsiloxane copolymer, mass average molecular weight: 60,000, proportion of methylhydrosiloxane: 6 mol %
  HMS-301: trade name, methylhydrosiloxane-dimethylsiloxane copolymer, mass average molecular weight: 2,000, proportion of methylhydrosiloxane: 27 mol %
  HMS-501: trade name, methylhydrosiloxane-dimethylsiloxane copolymer, mass average molecular weight: 1,100, Si—H equivalent amount: 135 g/mol
  HMS-991: trade name, methylhydrosiloxane polymer, mass average molecular weight: 1,600, Si—H equivalent amount: 67 g/mol
  HPM-502: trade name, methylhydrosiloxane-phenylmethylsiloxane copolymer, mass average molecular weight: 4,500, Si—H equivalent amount: 165 g/mol

[Silica Particles (C)]
Fumed silica: AEROSIL (trade name) series manufactured by NIPPON AEROSIL CO., LTD. (described in the Tables above with omitting "AEROSIL")
  AEROSIL RX300: trade name, average primary particle size: 7 nm, hexamethyldisilazane (HMDS) surface treated
  AEROSIL RX200: trade name, average primary particle size: 12 nm, HMDS surface treated
  AEROSIL RX380S: trade name, average primary particle size: 5 nm, HMDS surface treated
  AEROSIL R976S: trade name, average primary particle size: 7 nm, dimethyldichlorosilane (DDS) surface treated
  AEROSIL 300: trade name, average primary particle size: 7 nm, no surface treatment
  AEROSIL 200: trade name, average primary particle size: 12 nm, no surface treatment Dry silica by burning method: HDK (trade name) series manufactured by Wacker asahikasei silicone co., ltd. (described in the Tables above with omitting "HDK") HDK H 20: trade name, average primary particle size: 10 nm, HMDS surface treated As shown in Tables 1 to 3, the silicone resins for an acoustic-wave probe according to Examples 1 to 12 each was excellent in resin hardness, tensile strength at break, tear strength and resistance to abrasion, while maintaining at least −72 dB of acoustic (ultrasonic) sensitivity. Further, the silicone resins for an acoustic-wave probe according to Examples 13 to 18, in which silicone had phenyl groups, were excellent in acoustic (ultrasonic) sensitivity, resin hardness, tensile strength at break, tear strength, and resistance to abrasion, and had a high acoustic impedance. Among them, the silicone resins for an acoustic-wave probe according to Examples 15 to 18, in which both of the polyorganosiloxanes (A) and (B) had phenyl groups, had an improved acoustic impedance. In contrast, the silicone resins for an acoustic-wave probe according to Comparative Examples 1 to 3 each did not achieve an adequate tear strength and an adequate resistance to abrasion.

From these results, it is found that the composition for an acoustic-wave probe according to the present invention is useful as a member of medical devices. Further, the silicone resin of the present invention can be favorably used for an acoustic lens and/or an acoustic matching layer of an acoustic-wave probe, and also for a device for measuring an acoustic wave and an ultrasonic diagnosis device. In particular, the composition for an acoustic-wave probe and the silicone resin for an acoustic-wave probe can be favorably used for the purpose of improving sensitivity in an ultrasonic probe which uses cMUT as a transducer allay for ultrasonic diagnosis, a device for measuring a photo acoustic wave and an ultrasonic endoscope.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Acoustic lens
2 Acoustic matching layer
3 Piezoelectric element layer
4 Backing material
7 Chassis
9 Code
10 Ultrasonic search unit (probe)

The invention claimed is:

1. An acoustic-wave probe, comprising at least one selected from the group consisting of an acoustic lens and an acoustic matching layer, which comprise a silicone resin for an acoustic-wave probe, in which a composition for an acoustic-wave probe is hardened,
the composition for an acoustic-wave probe comprising a polysiloxane mixture, and wherein the polysiloxane mixture comprises: a polysiloxane having a vinyl group; a polysiloxane having at least two Si—H groups in the molecular chain thereof; and silica particles having an average primary particle size of less than 12 nm.

2. A device for measuring an acoustic wave, comprising the acoustic-wave probe according to claim 1.

3. An ultrasonic diagnosis device, comprising the acoustic-wave probe according to claim 1.

4. The acoustic-wave probe according to claim 1,
wherein the polysiloxane mixture comprises from 0.1 to 30 parts by mass of the silica particles having an average primary particle size of less than 12 nm, in a total amount of 100 parts by mass of the polysiloxane mixture.

5. The acoustic-wave probe according to claim 1
wherein the polysiloxane mixture comprises, in a total amount of 100 parts by mass thereof:
from 10 to 99.4 parts by mass of the polysiloxane having a vinyl group; and
from 0.5 to 90 parts by mass of the polysiloxane having at least two Si—H groups in the molecular chain thereof.

6. The acoustic-wave probe according to claim 1,
wherein the silica particles having an average primary particle size of less than 12 nm has a surface treated with a silane compound.

7. The acoustic-wave probe according to claim 1,
wherein the silica particles having an average primary particle size of less than 12 nm has a surface treated with a trimethylsilylation agent.

8. The acoustic-wave probe according to claim 1,
wherein the polysiloxane having a vinyl group comprises a phenyl group.

9. The acoustic-wave probe according to claim 1,
wherein the polysiloxane having a vinyl group has a mass-average molecular weight from 10,000 to 200,000.

10. The acoustic-wave probe according to claim 1,
wherein the polysiloxane having a vinyl group has a mass-average molecular weight from 30,000 to 150,000.

11. The acoustic-wave probe according to claim 1,
wherein the polysiloxane having at least two Si—H groups in the molecular chain thereof comprises a phenyl group.

12. The acoustic-wave probe according to claim 1,
wherein the composition for an acoustic-wave probe comprises from 0.00001 to 0.01 parts by mass of platinum or a platinum compound, with respect to 100 parts by mass of the polysiloxane mixture.

13. An ultrasonic probe, comprising:
a capacitive micromachined ultrasonic transducer as an ultrasonic transducer array; and
an acoustic lens comprising a silicone resin for an acoustic-wave probe,
in which a composition for an acoustic-wave probe is hardened,
the composition for an acoustic-wave probe comprising a polysiloxane mixture, and wherein the polysiloxane mixture comprises: a polysiloxane having a vinyl group; a polysiloxane having at least two Si—H groups in the molecular chain thereof; and silica particles having an average primary particle size of less than 12 nm.

14. A device for measuring a photo acoustic wave, comprising an acoustic lens comprising a silicone resin for an acoustic-wave probe, in which a composition for an acoustic-wave probe is hardened,
the composition for an acoustic-wave probe comprising a polysiloxane mixture, and wherein the polysiloxane mixture comprises: a polysiloxane having a vinyl group; a polysiloxane having at least two Si—H groups in the molecular chain thereof; and silica particles having an average primary particle size of less than 12 nm.

15. An ultrasonic endoscope, comprising an acoustic lens comprising the silicone resin for an acoustic-wave probe, in which a composition for an acoustic-wave probe is hardened,
the composition for an acoustic-wave probe comprising a polysiloxane mixture, and wherein the polysiloxane mixture comprises: a polysiloxane having a vinyl group; a polysiloxane having at least two Si—H groups in the molecular chain thereof; and silica particles having an average primary particle size of less than 12 nm.

* * * * *